United States Patent [19]
Biedermann et al.

[11] Patent Number: 5,114,954
[45] Date of Patent: May 19, 1992

[54] ANTIINFLAMMATORY BENZYLSELENOBENZAMIDES FROM AMINOPYRIDINES AND PICOLYLAMINES

[75] Inventors: Jürgen Biedermann, Pulheim, Fed. Rep. of Germany; Michel Evers, Liege, Belgium; Rolf Terlinden, Cologne, Fed. Rep. of Germany; Sigurd Leyck, Pulheim, Fed. Rep. of Germany; Erich Graf, Kerpen-Horrem, Fed. Rep. of Germany

[73] Assignee: A. Nattermann & Cie. GmbH, Cologne, Fed. Rep. of Germany

[21] Appl. No.: 611,275

[22] Filed: Nov. 8, 1990

[30] Foreign Application Priority Data

Nov. 8, 1989 [DE] Fed. Rep. of Germany ....... 3937170

[51] Int. Cl.$^5$ .................. C07D 213/24; A61K 31/64
[52] U.S. Cl. .................... 514/338; 514/344; 514/349; 514/351; 514/352; 514/357; 546/270; 546/286; 546/289; 546/297; 546/300; 546/309; 546/330; 546/337
[58] Field of Search ............... 546/286, 289, 297, 300, 546/270, 309, 330, 337; 514/338, 344, 349, 351, 352, 357

[56] References Cited

U.S. PATENT DOCUMENTS

4,730,053  3/1988  Dereu et al. .................. 546/335

FOREIGN PATENT DOCUMENTS

3443467  5/1986  Fed. Rep. of Germany.
3626554  2/1988  Fed. Rep. of Germany.

OTHER PUBLICATIONS

Weber et al., "3-Chloro-1,2-Benzisoselenazolium ...", CA 85: 192626h, 1976.
Welter et al., "Benzisoselenazolinones ...", CA 96: 199699v (1982).

*Primary Examiner*—C. Warren Ivy
*Assistant Examiner*—Celia Chang
*Attorney, Agent, or Firm*—Herbert Dubno

[57] ABSTRACT

Benzylselenobenzamides of formula I

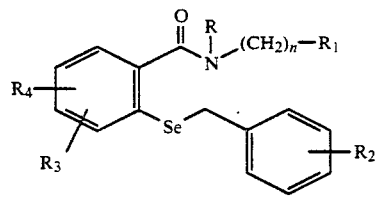

with inflammation-inhibiting characteristics and used in pharmaceutical preparations.

5 Claims, No Drawings

ANTIINFLAMMATORY BENZYLSELENOBENZAMIDES FROM AMINOPYRIDINES AND PICOLYLAMINES

FIELD OF THE INVENTION

The invention relates to novel benzylselenobenzamides, methods and intermediates for their preparation and pharmaceutical products containing these compounds.

DESCRIPTION OF THE INVENTION

The compounds to which this invention relates correspond to the formula I

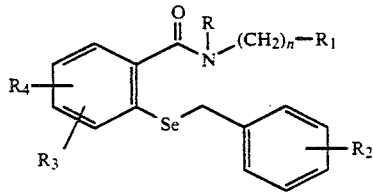

where
- R is hydrogen, ethyl or methyl and
- $R_1$ represents the 2-, 3-, or 4-pyridyl group which can be substituted with fluorine, chlorine, bromine, $C_{1-4}$-alkyl, $C_{1-4}$-alkoxy, hydroxy, cyano, amino, dimethylamino or nitro and
- $R_2$, $R_3$ and $R_4$ are identical or different and, taken separately, represent hydrogen, fluorine, chlorine, bromine, trifluoromethyl, $C_{1-4}$-alkyl, $C_{1-4}$-alkoxy, hydroxy, cyano or nitro or
- $R_3$, $R_4$ taken together, represent methylenedioxy and n is zero or 1.

Especially preferred are compounds of the formula I in which n equals zero and R and $R_2$ represent hydrogen, $R_1$ is the pyridyl group and $R_3$ and $R_4$ are identical or different and, taken separately, represent hydrogen, fluorine, chlorine, bromine, trifluoromethyl, methyl, methoxy, hydroxy, cyano or nitro or $R_3$ and $R_4$, taken together, represent methylenedioxy.

Also preferred are compounds of the formula I in which n equals 1 and R and $R_2$ represent hydrogen, $R_1$ is an unsubstituted pyridyl residue and $R_3$ and $R_4$ are identical or different and, taken separately, represent hydrogen, fluorine, chlorine, bromine, trifluoromethyl, methyl, methoxy, hydroxy, cyano or nitro or $R_3$ and $R_4$, taken together, represent methylenedioxy.

Examples of compounds to which the invention relates are:
- 2-Benzylseleno-N-(2-pyridyl)benzamide
- 2-Benzylseleno-N-(3-pyridyl)benzamide
- 2-Benzylseleno-N-(4-pyridyl)benzamide
- 2-Benzylseleno-N-(2-picolyl)benzamide
- 2-Benzylseleno-N-(3-picolyl)benzamide
- 2-Benzylseleno-N-(4-picolyl)benzamide
- 2-(Benzylseleno)-N-(3-pyridyl)-trifluoromethylbenzamide
- 2-(Benzylseleno-3-fluoro-N-(3-pyridyl) -benzamide.

These compounds are effective anti-inflammatories and can be administered topically, enterally, parenterally and by intravenous, subcutaneous or intramuscular injection.

The compounds to which the invention relates can either be prepared from the corresponding 2-benzylselenobenzoic acid of formula II

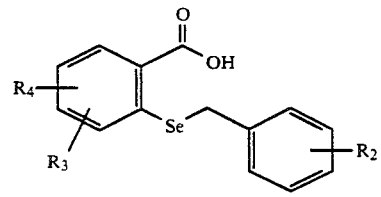

by reaction in a chlorinated hydrocarbon with chloromethylenedimethyliminium chloride (Vilsmeier's reagent)—according to reaction scheme 1—and the pyridyl or picolyl compound with which it is to be reacted or by reaction of the imidazoline of the acid (according to reaction scheme 2) with a pyridylamine or picolylamine.

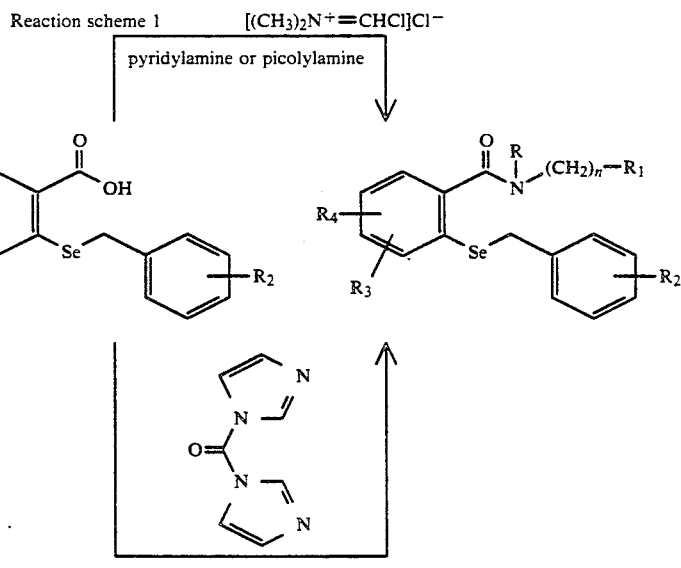

Reaction scheme 1     $[(CH_3)_2N^+=CHCl]Cl^-$

Reaction scheme 2     pyridylamine or picolylamine

Another route leads via the reaction of a compound of formula II with 2-chloro-1-methylpyridinium iodide reaction scheme 3) and a pyridine-containing amine.

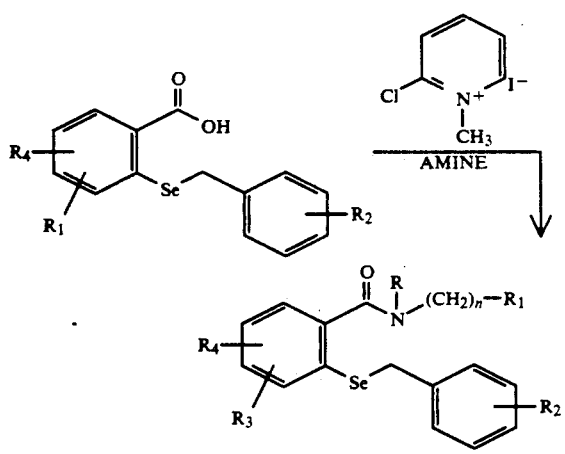

Suitable starting products for the synthesis of the compounds to which the invention relates are, for instance:
2-Benzylselenobenzoic acid
2-(4-Methylbenzylseleno)benzoic acid
2-(4-Methoxybenzylseleno)benzoic acid
2-(4-Bromobenzylseleno)benzoic acid
2-(4-Cyanobenzylseleno)benzoic acid
2-(4-Nitrobenzylseleno)benzoic acid
2-(4-Fluorobenzylseleno)benzoic acid
2-(4-Chlorobenzylseleno)benzoic acid
2-Benzylseleno-3-methoxybenzoic acid
2-Benzylseleno-3-fluorobenzoic acid
2-Benzylseleno-3,4-methylenedioxybenzoic acid
2-Benzylseleno-3-trifluoromethylbenzoic acid and
2-Benzylseleno-4-methylbenzoic acid.

This invention also relates to pharmaceutical products containing compounds according to formula I as active ingredients. Pharmaceutical products to which the invention relates are enteral as well as oral, rectal or parenteral dosage forms which contain the pharmaceutical active ingredient either alone or together with a usual, pharmaceutically employed excipient. The pharmaceutical preparations of the active ingredient should preferably take the form of individual doses, which are adapted to the desired method of administration, such as, for example, tablets, dragees, capsules, suppositories, granules, solutions, emulsions or suspensions The dosage of substance usually lies between 10 and 1000 mg/day, preferably between 30 and 300 mg/day, and can be administered in one dose or distributed over several doses, preferably over two or three doses daily. It has been discovered that these pharmaceutical products have excellent inflammation inhibiting characteristics. The preparation of the substances to which the invention relates will be elucidated in more detail in the examples that follow.

The melting points quoted were determined using a Buchi 510 melting point determination apparatus and are quoted in °C. and have not been corrected.

EXAMPLE 1

2-Benzylselenobenzoic acid

To a stirred suspension of 50.0 g (0.125 mol) diselenosalicylic acid in 380 ml water is added 38.0 g (0.95 mol) sodium hydroxide, when the internal temperature rises to 45° C. and the acid goes into solution. On addition of 100 g (0.94 mol) sodium carbonate and 58 g (0.333 mol) sodium dithonite the temperature increases to 55° C. The mixture is heated to reflux for 2 h, allowed to cool to room temperature and 47.6 ml (68.4 g; 0.4 mol) benzyl bromide is added dropwise within 10 minutes. A further 100 ml water is added and the mixture stirred for another 14 h at room temperature, then 355 ml (32%) hydrochloric acid is added to the reaction mixture with stirring, the precipitated white solid is filtered off and washed to neutrality with water.

The moist product is recrystallized from 1600 ml 2-propanol with the addition of 3 g active charcoal. The yield is 48.8 g (67% of th.). The mother liquors yield a further 12 g (16.5%) 2-benzylselenobenzoic acid.

Yield 60.8 g (83.5% of th.)
mp 209°–210° C.

EXAMPLE 2

2-Benzylseleno-N-(2-pyridyl)benzamide 2.94 g (0.0086 mol) 2-benzylselenobenzoic acid imidazolide (prepared from 2-benzylselenobenzoic acid and N, N'-carbonyldiimidazole in tetrahydrofuran) and 0.81 g (0.0086 mol) 2-aminopyridine are dissolved in 20 ml dimethylformamide and heated to 150° C. for 14 h. Then 200 ml water is added and the oily reaction product extracted with two 50 ml portions of dichloromethane. The organic phase is dried, the solvent removed and recrystallized successively from 2-propanol (20 ml) and toluene (20 ml).

A residual content of 2-benzylselenobenzoic acid is removed by crushing the crystals, stirring with 1N NaOH (50 ml), washing until neutral and recrystallizing from 2-propanol (20 ml).

Yield 0.65 g (20.6% of th.)
mp 134°–135° C.

EXAMPLE 3

2-Benzylseleno-N-(3-pyridyl)benzamide

To a stirred suspension of 5.82 g (0.02 mol) 2-benzylselenobenzoic acid in 30 ml dichloromethane which has been cooled to −5° C. is added 2.82 g (0.022 mol) chloromethylenedimethyliminium chloride and stirring is continued for 2 hours at room temperature. Then a solution of 2.07 g (0.022 mol) 3-aminopyridine and 4.79 g (0.047 mol) triethylamine in 30 ml dichloromethane is added dropwise within 10 minutes and the mixture is stirred for 14 hours and then extracted with 50 ml water. The solid that dissolves neither in water nor dichloromethane (hydrochloride of the reaction product) is filtered off, suspended in a mixture of 60 ml ethyl acetate, 40 ml diethyl ether and 2 ml ethanol and stirred with 50 ml 1N NaOH. The organic phase is separated off, washed with water until neutral, dried, the solvent removed and recrystallized from 2-propanol (60 ml).

Yield 3.0 g (40.8% of th.)
mp 151°–153° C.

EXAMPLE 4

2-Benzylseleno-N-(4-pyridyl)benzamide

To a solution of 2.91 g (0.01 mol) 2-benzyl -selenobenzoic acid (from example 1) and 1.4 ml (0.01 mol) triethylamine in 25 ml dichloromethane is added 2.56 g (0.01 mol) 2-chloro-1-methylpyridinium iodide and the mixture is stirred for 1 h. Then a solution of 0 94 g (0.01 mol) 4-aminopyridine and 1.4 ml (0.01 mol) triethylamine in 25 ml dichloromethane is added and stirring continued for 2 hours. The mixture is then extracted with two 50 ml portions of water, dried and the solvent removed. The product is finally recrystallized from 2-propanol (40 ml)/n-hexane (40 ml).

Yield 1.8 g (49% of th.)
mp 58° C.

EXAMPLE 5

2- Benzylseleno-N-(2-picolyl)benzamide

To a stirred suspension of 4.0 g (0.0137 mol) 2-benzylselenobenzoic acid (example 1) in 20 ml dichloromethane, which has been cooled to 10° C., is added 1.8 g (0.0146 mol) chloromethylenedimethyliminium chloride (Vilsmeier's reagent) and the mixture stirred for 2 hours. Then a solution of 1.49 g (0.0138 mol) 2-picolylamine and 3.0 g (0.03 mol) triethylamine in 10 ml dichloromethane is added dropwise within 10 minutes and the mixture is stirred for 14 hours. It is then extracted successively with 50 ml water, 50 ml 1N NaOH, 50 ml (5%) acetic acid and 50 ml water, the dichlormethane phase is dried, the solvent removed and the residue recrystallized twice from 60 ml portions of 2-propanol.

Yield 3.48 g (66.6 % of th)
mp 141°-142° C.

EXAMPLE 6

2-Benzylseleno-N-(3-picolyl)benzamide

Repeating the procedure in example 5 but using: 4.0 g (0.0137 mol) 2-benzylselenobenzoic acid (example 1)
1.49 g (0.0138 mol) 3-picolylamine
Yield 2.84 g (54.4% of th.)
mp 156°-157° C.

EXAMPLE 7

2-Benzylseleno-N-(4-picolyl)benzamide

Repeating the procedure in example 5 but using: 4.0 g (0.0137 mol) 2-benzylselenobenzoic acid (example 1)
1.49 g (0.0138 mol) 4-picolylamine
Yield 1.52 g (29.1% of th.)
mp 151°-152° C.

EXAMPLE 8

4,4-Dimethyl-2-(2-benzylseleno-3-fluorophenyl)-1,3,oxazoline

To a solution of 30.0 g 4,4-dimethyl-2-(3-fluorophenyl)-1,3-oxazoline in 400 ml anhydrous tetrahydrofuran, which has been cooled to −45° C., is added dropwise 100 ml of a 1.6 molar solution of n-butyllithium in n-hexane in such a manner that the temperature does not rise over −40° C. (25 min.) After stirring for 2 hours at −45° C. the reaction mixture is warmed to 0° C. and then treated dropwise with a solution of 54.7 g (0.16 mol) dibenzyl diselenide in 250 ml anhydrous tetrahydrofuran within 20 min. The reaction mixture is stirred for 18 hours at room temperature. The contents of the flask are transferred to 300 g ice and 300 ml water and extracted twice with 300 ml portions of diethyl ether. The organic phase is extracted successively with 200 ml water, 200 ml 10% sodium hydrogen carbonate solution and 200 ml water, dried over sodium sulfate and the solvent removed in vacuum. The crude product (58.3 g) is cleaned up by column chromatography (silica gel/dichloromethane).

Yield 43.5 g (75% of th.)
mp 95° C.

EXAMPLE 9

2-Benzylseleno-3-fluorobenzoic acid

A suspension of 43.5 g (0.12 mol) 4,4-dimethyl-2-(2-benzylseleno-3-fluorophenyl)-1,3-oxazoline in 102.6 g (0.6 mol) benzyl bromide is stirred at room temperature for 24 hours and the solvent removed. The residue is dissolved in a mixture of 1.8 l 20% NaOH and 1.8 l methanol, heated under reflux for 12 hours and the reaction mixture extracted with 300 ml diethyl ether. The aqueous phase is adjusted to pH 1 with conc. HCl and the precipitated solid filtered off, washed with 200 ml water and dried. After the extraction the ethereal residue is dissolved once more in benzyl bromide and treated as described above. After adjusting the aqueous solution to pH 1 the precipitate is first washed with water and then, after drying, with n-hexane.

Total Yield 29.9 g (80.6% of th.)
mp 137°-138° C.

EXAMPLE 10

2-Benzylseleno-3-fluoro-N-(3-pyridyl)benzamide

To a solution of 14.5 g (0.047 mol) 2-benzylseleno-3-fluorobenzoic acid and 6.54 ml triethylamine in 90 ml dichloromethane which has been cooled to 0° C. is added 11.9 g (0.047 mol) solid bis(2-oxo-3-oxazolidinyl)-phosphoryl chloride in one portion. After 10 minutes stirring 4.42 g (0.047 mol) 3-aminopyridine in 40 ml dichloromethane is added dropwise at room temperature followed after stirring for another 15 minutes by 6.54 ml triethylamine in 20 ml dichloromethane. After 48 h at room temperature the reaction mixture is washed with 150 ml water and the organic phase is extracted successively with 100 ml 2N NaOH, 100 ml 10% HCl and 100 ml water. The organic phase is dried over sodium sulfate, then concentrated under water pump vacuum and filtered through a column (silica gel/dichloromethane). The concentrated, cleaned-up fractions are then recrystallized from 350 ml of a mixture of dichloromethane (8:2).

Yield 10.2 g (57% of th.)
mp 130°-131° C.

We claim:

1. A benzylselenobenzamide of the formula

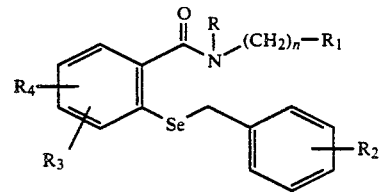

where
R is hydrogen, methyl or ethyl and
$R_1$ represents the 2-, 3-, or 4-pyridyl group which can be substituted with fluorine, chlorine, bromine, $C_{1-4}$alkyl, $C_{1-4}$-alkoxy, hydroxy, cyano, amino, dimethylamino or nitro and
$R_2$, $R_3$ and $R_4$ are identical or different and, taken separately, represent hydrogen, fluorine, chlorine, bromine, trifluoromethyl, $C_{1-4}$-alkyl, $C_{1-4}$-alkoxy, hydroxy, cyano or nitro or
$R_3$, $R_4$ taken together, represent methylenedioxy and n is zero or 1.

2. A benzylselenobenzamide according to claim 1 wherein n equals zero and R and $R_2$ represents hydrogen.

3. A benzylselenobenzamide according to claim 1 wherein n equals 1 and R and $R_2$ represent hydrogen.

4. A pharmaceutical composition having inflammation-inhibiting characteristics comprising:
   (i) an active ingredient present in an effective amount to inhibit inflammation, said active ingredient having a formula I

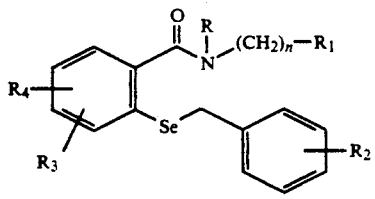

where
R is hydrogen, methyl or ethyl and
$R_1$ represents the 2-, 3-, or 4-pyridyl group which can be substituted with fluorine, chlorine, bromine, $C_{1-4}$-alkyl, $C_{1-4}$-alkoxy, hydroxy, cyano, amino, dimethylamino or nitro and
$R_2$, $R_3$ and $R_4$ are identical or different and, taken separately, represent hydrogen, fluorine, chlorine, bromine, trifluoromethyl, $C_{1-4}$-alkyl, $C_{1-4}$-alkoxy, hydroxy, cyano or nitro or
$R_3$, $R_4$ taken together, represent methylenedioxy and
n is zero or 1; and (ii) a pharmaceutically acceptable carrier present in an amount effective to deliver said active ingredient.

5. A method for treating inflammation in a subject susceptible to inflammation comprising administering to said subject in an effective dosage an effective amount of an active ingredient in combination with an effective amount to deliver said active ingredient of a pharmaceutically acceptable carrier, said active ingredient being a benzylselenobenzamide of the formula I

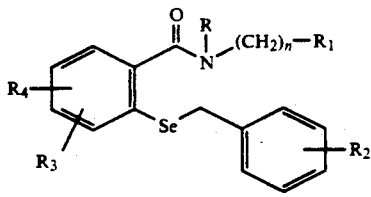

where
R is hydrogen, methyl or ethyl and
$R_1$ represents the 2-, 3- or 4-pyridyl group which can be substituted with fluorine, chlorine, bromine, $C_{1-4}$-alkyl, $C_{1-4}$-alkoxy, hydroxy, cyano, amino, dimethylamino or nitro and
$R_2$, $R_3$ and $R_4$ are identical or different and, taken separately, represent hydrogen, fluorine, chlorine, bromine, trifluoromethyl, $C_{1-4}$-alkyl, $C_{1-4}$-alkoxy, hydroxy, cyano or nitro or
$R_3$, $R_4$ taken together, represent methylenedioxy and
n is zero or 1.

* * * * *